(12) United States Patent
Holmes et al.

(10) Patent No.: US 6,693,159 B1
(45) Date of Patent: Feb. 17, 2004

(54) MANUFACTURING POROUS CROSS-LINKED POLYMER MONOLITHS

(75) Inventors: Andrew Bruce Holmes, Cambridge (GB); Andrew Ian Cooper, Liverpool (GB)

(73) Assignee: Cambridge University Technical Services Limited (GB)

( * ) Notice: Subject to any disclaimer, the term of this patent is extended or adjusted under 35 U.S.C. 154(b) by 0 days.

(21) Appl. No.: 09/890,630

(22) PCT Filed: Feb. 7, 2000

(86) PCT No.: PCT/GB00/00347

§ 371 (c)(1),
(2), (4) Date: Sep. 28, 2001

(87) PCT Pub. No.: WO00/46281

PCT Pub. Date: Aug. 10, 2000

(30) Foreign Application Priority Data

Feb. 5, 1999 (GB) .......................................... 99024630

(51) Int. Cl.[7] .............................................. C08F 120/10
(52) U.S. Cl. ................. 526/323.1; 526/323.2; 526/336; 526/942
(58) Field of Search .............................. 526/942, 323.1, 526/323.2, 336

(56) References Cited

U.S. PATENT DOCUMENTS

| | | | | | |
|---|---|---|---|---|---|
| 5,629,353 | A | * | 5/1997 | Steckle et al. ................. | 521/64 |
| 5,679,737 | A | * | 10/1997 | DeSimone .................. | 524/529 |
| 5,780,565 | A | | 7/1998 | Clough et al. | |
| 5,840,820 | A | | 11/1998 | DeSimone et al. | |
| 6,057,409 | A | * | 5/2000 | Cunningham et al. ...... | 526/201 |
| 6,303,666 | B1 | * | 10/2001 | Yorita .......................... | 521/79 |
| 6,376,059 | B1 | * | 4/2002 | Anderson et al. ......... | 428/314.8 |

* cited by examiner

*Primary Examiner*—Bernard Lipman
(74) *Attorney, Agent, or Firm*—Saliwanchik, Lloyd & Saliwanchik

(57) ABSTRACT

Highly cross-linked, maroporous/mesoporous polymer monoliths are prepard using supercritical carbon dioxide ($scCO_2$) as the solvent and porogen for the polymerisation of monomers having more than one polymerisable group, at a monomer concentration in $CO_2$ of more than 40 vol %. The procedure allows the direct formation of dry, solvent-free, macroporous/mesoporous cross-linked monoliths with large surface area and well-controlled pore size distribution.

8 Claims, No Drawings

MANUFACTURING POROUS CROSS-LINKED POLYMER MONOLITHS

FIELD OF THE INVENTION

The present invention relates to the synthesis of highly cross-linked polymers in $scCO_2$, i.e. supercritical carbon dioxide.

BACKGROUND OF THE INVENTION

Macroporous cross-linked polymer resins are usefull in a wide range of applications, including solid-phase synthesis, combinatorial chemistry, polymer-supported reagents, molecular imprinting, and size-exclusion chromatography. In the past, it has been common to produce these cross-linked polymer resins either as irregular particles or microspherical beads by heterogeneous polymerisation techniques such as suspension, emulsion, precipitation, and dispersion polymerisation; see Arshady, Colloid Polym. Sci. (1992) 270:717. More recently, it has become clear that, for certain applications, there are distinct advantages in producing cross4inked polymer resins in the form of highly porous continuous blocks, or 'monoliths'; see Svec et al., Science (1996) 273:205; Peters et al., Anal. Chem. (1997) 69:3646; and also the review by Peters et al, Adv. Materials (1999) 11(14):1169.

Supercritical carbon dioxide ($scCO_2$) is an attractive solvent for polymer chemistry because it is inexpensive, non-toxic, and non-flammable. Unlike conventional liquid solvents, $scCO_2$ is highly compressible and the density (and therefore solvent properties) can be tuned over a wide range by varying pressure. Moreover, $scCO_2$ reverts to the gaseous state upon depressurisation, greatly simplifying the separation of solvent from solute(s). $scCO_2$ has been used as a solvent medium for homogeneous polymerisations [DeSimone et al., Science (1992) 257:945; and PCT/US93/01626] and heterogeneous precipitation polymerisations [Romack et al., Macromolecules (1995) 28:912]. Polymeric surfactants or stabilisers have been developed, which allow the synthesis of $CO_2$-insoluble polymers in $scCO_2$ in high yields by dispersion polymerisation; see DeSimone et al., Science (1994) 265:356; Canelas et al., Macromolecules (1997) 30:5673; and U.S. Pat. No. 5,679,737. All of these examples relate to the polymerisation in $scCO_2$ of monomers containing a single polymerisable functional group (e.g., styrene, methyl methacrylate, acrylic acid).

DE-A-3609829 and U.S. Pat. No. 4,748,220 disclose forming cross-linked polymer particles in liquid or supercritical $CO_2$. The polymers were formed as non-porous pulverent powders with primary particles in the size range 0.5–3 μm.

U.S. Pat. No. 5,629,353 describes the use of a range of supercritical fluid solvents in various stages of the processing and/or formation of cross-linked nanoporous polymers. Their use in preparing microcellular cross-linked foams is described in U.S. Pat. Nos. 5,128,382, 5,252,620, and 5,066,684.

Cooper et al., Macromol. Rapid Commun. (1998) 19:353, describes the formation of regular non-porous cross-linked poly(divinyl benzene) microspheres in supercritical $CO_2$ by heterogeneous polymerisation, both with and without the use of polymeric surfactants. This work is also disclosed in WO-A-99/38820 (published after the priority date claimed herein), where it is suggested that the polymerisation of divinylbenzene, trimethylolpropanetrimethacrylate or ethylene glycol dimethacrylate may be conducted, optionally with a copolymerisable monomer and optionally in the presence of a surfactant, at a monomer concentration of 15–40% vol % in $CO_2$. In the Examples, the monomer concentration is 20 vol %.

SUMMARY OF THE INVENTION

The present invention is based on the discovery that a range of cross-linked polymers can be formed using $scCO_2$ as the polymerisation medium, using multi-functional monomers containing two or more polymerisable functional groups, and that the polymers can be isolated in high yields directly from the reaction vessel as dry materials, surprisingly in the form of macroporous/mesoporous polymer monoliths with variable, well-controlled pore size distributions. The concentration of the monomer in $CO_2$ should be above 40 vol %.

The pore size of the polymer monolith can be tuned, by varying the monomer concentration and/or by varying the $CO_2$ density. It may also be tuned by conducting the polymerisation in the presence of a water-in-$CO_2$ emulsion.

The cross-linked polymers are useful in a variety of potential applications, including molecular imprinting, solid phase synthesis, combinatorial chemistry, polymer-supported reagents, size exclusion chromatography, and supercritical fluid chromatography.

DESCRIPTION OF THE INVENTION

The process of the invention provides porous cross-linked polymer monoliths, preferably using volume percentages of monomer-in-$CO_2$ in the range 40–60%, most preferably in the range 50–60%. The cross-linked polymers can be isolated as dry, macroporous/mesoporous monoliths, directly from the reactor. Since the solvent, $CO_2$, reverts to a gas upon depressurisation, no solvent residues are left in the resulting cross-linked polymers and the use of VOC solvents is avoided.

The most preferred monomers are trimethylol propane trimethacrylate and ethylene glycol dimethacrylate. Another suitable monomer is divinylbenzene. Other suitable cross-linking agents are $CO_2$-soluble bi-/multi-functional methacrylate monomers, bi-/multi-functional acrylate monomers, bi-/multi-functional allyl ether monomers, bi-/multi-functional epoxide monomers, bi-/multi-functional oxetane monomers, and bi-/multi-functional isocyanate monomers.

Highly cross-linked copolymers may be obtained by copolymerisation using the cross-linker with comonomers that contain reactive functional groups. Suitable comonomers include methacrylate and acrylate-based comonomers containing alkyl fluoroalkyl, poly(dimethyl siloxane) chains, low molecular weight poly(ethylene glycol) chains, perfluoropolyetherchains, alkyl halides, acid halides (e.g., methacryloyl chloride), alcohols (alkyl and aryl), protected alcohols (alkyl and aryl), esters (alkyl and aryl), aldehydes (alkyl and aryl), amines (alkyl and aryl), amides (alkyl and aryl), crown ethers, porphyrins, template groups for molecular imprinting, hygroscopic groups for the formation of superabsorbent polymers, functional groups for affinity chromatography, derivatisable functional groups for parallel synthesis, organic dyes, inorganic/organic reagents for organic synthesis, and transition metal/main group metal catalysts. Preferably, the comonomer includes a carboxylic acid group, e.g. methacrylic acid. The proportion of any such comonomer will typically be from 10 to 80%, preferably up to 50%, and more preferably 20%, w/w of the total monomers.

The polymerisation procedure works efficiently in $scCO_2$ when thermal free radical initiation is used, employing 2,2'-azobisisobutyronitrile (AIBN) as the preferred initiator, e.g. at 50° C. Other initiators that may be used are other free radical initiators (either thermally or photochemically decomposed), and cationic initiators in the case of ring-opening polymerisations of oxirane/oxetane based cross-linking monomers.

The cross-linked polymer monoliths are formed as continuous porous rods which conform to the cylindrical shape of the internal reactor volume. Continuous macroporous monoliths may also be formed (or 'moulded') in other high-pressure vessels, such as wide-bore chromatography columns and narrow-bore silica/PEEK capillaries, in order to form novel continuous chromatography packings.

Carbon dioxide acts as an efficient, non-solvating porogenic solvent for the introduction of porosity in the polymer monoliths. The average pore diameter and pore size distribution can be varied over a wide range by changing the volume ratio of monomer to carbon dioxide; see in particular Table 2. The Examples show that an increase in the $CO_2$-to-monomer ratio leads to larger pore sizes for the resultant polymers. Furthermore, the polymers can have relatively narrow and unimodal pore size distributions.

The monolithic polymers may subsequently be derivatised by covalent reactions such as nucleophilic, electrophilic, radical substitution or addition)or grafting reaction), or non-covalent bonding (electrostatic interactions, H-bonding, pi-pi stacking) with additional chemical functionality by passing chemical reagents through the porous channels, either as solutions in organic solvents or as solutions in supercritical $CO_2$. This is advantageous, particularly in cases where conventional derivatisation techniques employing reactive hydrophilic or aqueous solvents are incompatible with the desired chemical functionality or polymer matrix.

In one embodiment of the invention, the polymerisation is carried out directly within a chromatography column in order to form a chromatographic packing material in situ. This may be for separations where the solvent is compressed $CO_2$ or a conventional aqueous or non-aqueous solvent.

In another embodiment, the monolith is chemically derivatised by flowing a solution of a chemical reagent in a solvent through the porous material. This solvent may be $scCO_2$ or a conventional aqueous or non-aqueous solvent.

Monoliths produced according to the invention have a variety of uses. For example, such a monolith may be used as a support for solid phase synthesis, as a support for polymeric reagents and scavengers, for solid phase extraction, for solid phase detection, for high-throughput screening, for on-chip separations, for molecular imprinting, for molecular recognition, as a high throughput bioreactor, or as a stationary phase for high performance liquid chromatography, supercritical fluid chromatography, high performance membrane chromatography or capillary electrochromatography.

The following Examples illustrate the invention.

EXAMPLE 1

Trimethylol propane trimethacrylate (TPM) was purified by passage though a neutral alumina column. 2,2'-azobisisobutyronitrile (AIBN) was purified by recrystallising twice from methanol. The TPM (5.0 cm$^3$) and AIBN (0.1 g) were added to a 10 cm$^3$ stainless steel, high pressure reactor, equipped with a PTFE-coated magnetic stir bar, and a sapphire window for the observation of phase behaviour. The reactor was purged with a slow flow of $CO_2$ for 20 min, after which time the vessel was filled with liquid $CO_2$ (T=22° C., P=64 bar) and stirring was commenced using the stir bar. Under these initial conditions, the monomer and initiator were completely soluble in the $CO_2$ continuous phase. The reactor was heated to achieve the required polymerisation conditions (50° C., P=310±10 bar). Over time (c.20 minutes), an orange colour was observed in the cell, corresponding to light scattering by primary polymer particles (i.e., the Tyndall effect). After a further period (c.60 minutes after reaching reaction conditions), a white, translucent appearance was observed in the reaction vessel, corresponding to gelation of the monomer/$CO_2$ mixture. After another 60 minutes, the mixture had an opaque, white appearance. The reactor was left at 50° C. overnight, after which it was allowed to cool to around 40° C. At this temperature, the $CO_2$ was vented slowly whilst still under supercritical conditions. The polymer was removed from the reactor as a dry, white, continuous monolith (4.90 g, 92%). IR (KBr)/cm$^{-1}$: 2970, 1735, 1650, 1559, 1542, 1517, 1490, 1461, 1264, 1152. Surface area ($N_2$ adsorption, BET method): 290 m$^2$/g. Total intrusion volume for pores larger than 7 nm (mercury intrusion porosimetry): 0.949 mL/g. Average pore diameter=0.0302 µm. Absolute polymer density (helium pyknometry): 1.49 g/cm$^3$.

EXAMPLES 2 to 8

The procedure of Example 1 was repeated, using the same monomer (TPM), optionally with methacrylic acid (MAA) or ethylene glycol dimethacrylate (EDMA), at 50° C. for 23 h. The other reaction conditions are given in Table 1. The results, in terms of the product characteristics of the products, are given in Table 2.

It is evident from Examples 1, 2 and 5 at least that an increase in the monomer concentration leads to a marked decrease in the median pore size and a corresponding increase in the specific surface area. Mercury intrusion porosimetry shows that the pore size distributions for Examples 1 and 2 are unimodal and narrow, while the polymer formed using 60 vol % TPM (Example 5) had a broader distribution, consisting mainly of pores less than 100 nm in diameter. Following IUPAC definitions, the products of Examples 1 and 2 would be termed macroporous, while the product of Example 5 is predominantly macroporous but appears to contain a number of pores in the mesopore/micropore size range. Scanning electron microscopy shows that the product of Example 1 consisted of relatively large particles, fused together to form an open, porous structure, while the products of Examples 2 and 5 were found to contain much smaller primary particles fused together to form a network of narrower pores. Without wishing to be bound by theory, this variation in polymer structure may be rationalised by considering the mechanism of formation of the polymeric matrix. Carbon dioxide is a very poor solvent for most polymers, with the exception of certain amorphous fluoropolymers and polysiloxanes. In the context of the present invention, the monomer can be considered as a much better thermodynamic solvent for the growing polymer than $CO_2$. Polymer network phase separation might thereforebe expected to occur somewhat later in reactions involving higher monomer concentrations. Consequently, when phase separation does occur, the microgel particles that are formed remain relatively small and discrete, and are fused together by further polymerisation in the $CO_2$ phase. At lower monomer concentrations, the phase separation would be expected to occur at somewhat lower conversions. Again, microgel particles are formed, but in this case significantly more polymer is generated after phase separation in both the monomer-swollen microgel particles and in the $CO_2$ phase. This leads to growth of the particles and in-filling of small pores between particles, thus forming large, fused aggregates with relatively low surface areas. If the monomer concentration is reduced even further, to about 20 vol % TPM, the concentration of polymer becomes too low for the formation of the fused monoliths, and the microgel particles appear as a fine powder.

Similar trends may be observed for polymers synthesised from EDMA (Examples 6–8), although average pore diameters were somewhat larger and specific surface areas were correspondingly lower. Examples 6 and 7 exhibited bimodal pore size distributions, while Example 8 showed a narrow, unimodal distribution.

Example 4 illustrates the preparation of a functional porous monolith. This illustrates the utility of the invention in the formation of well-defined, non-covalently imprinted monoliths, particularly since $CO_2$ is a non-polar, aprotic solvent which, like perfluorocarbons, should not interfere with most template-comonomer interactions.

When Example 1 was repeated, using a water-in-$CO_2$ emulsion, stabilised by sodium bis(2-ethylhexyl) sulfosuccinate, the pore size distribution was significantly broader, and shifted to include a wide range of pores with much smaller diameters (median pore diameter=25 nm). This process allows the tuning of pore sizes and pore size distributions in the resulting monolithic products. Before polymer phase separation, a clear, transparent aqueous microemulsion was observed in the reaction vessel. Previously, it has been very difficult to form a stable aqueous microemulsion in pure SCCO2 without using highly fluorinated stabilisers.

TABLE 1

| Example | monomer(s) | volume % monomer in reaction mixture | pressure (±10 bar) | appearance of product | yield (%) |
| --- | --- | --- | --- | --- | --- |
| 1 | TPM | 50 | 310 | solid white monolith | 92 |
| 2 | TPM | 40 | 310 | crumbly white monolith | 89 |
| 3 | TPM | 50 | 155 | solid white monolith | 95 |
| 4 | 75% TPM/25% MAA | 50 | 310 | solid off-white monolith | 90 |
| 5 | TPM | 60 | 310 | solid white monolith | 98 |
| 6 | EDMA | 40 | 310 | crumbly white monolith | 92 |
| 7 | EDMA | 50 | 310 | solid white monolith | 93 |
| 8 | EDMA | 60 | 310 | solid white monolith | 95 |

TABLE 2

| Example | total intrusion volume (mL/g) | total pore area (m²/g) | median pore diameter (volume) (µm) | median pore diameter (area) (µm) | average pore diameter (4V/A) (µm) | bulk density (g/mL) | skeletal density (g/mL) | porosity (%) |
| --- | --- | --- | --- | --- | --- | --- | --- | --- |
| 1 | 0.95 | 125.59 | 0.10 | 0.0075 | 0.030 | 0.62 | 1.49 | 58.6 |
| 2 | 0.92 | 74.31 | 7.88 | 0.0050 | 0.049 | 0.49 | 0.88 | 55.0 |
| 3 | 0.95 | 103.67 | 0.19 | 0.0065 | 0.037 | 0.61 | 1.45 | 58 |
| 4 | 0.75 | 68.47 | 2.19 | 0.0047 | 0.044 | 0.64 | 1.23 | 48.0 |
| 5 | 0.53 | 157.19 | 0.02 | 0.0069 | 0.013 | 0.80 | 1.37 | 44 |
| 6 | 1.03 | 0.81 | 7.86 | 2.7145 | 5.056 | 0.43 | 0.76 | 43.9 |
| 7 | 0.91 | 62.42 | 1.09 | 0.0047 | 0.059 | 0.60 | 1.32 | 54.6 |
| 8 | 0.96 | 122.86 | 0.13 | 0.0060 | 0.031 | 0.61 | 1.50 | 68.0 |

What is claimed is:

1. A process for the polymerisation of a monomer having two or more polymerisable groups, optionally together with another copolymerisable monomer, to give a porous, monolithic cross-linked polymer, which comprises conducting the polymerisation in compressed $CO_2$ as a solvent, wherein the concentration of the monomer or monomers is more than 40 vol %.

2. The process, according to claim 1, wherein the monomer is divinylbenzene, ethylene glycol dimethacrylate or trimethylol propane trimethacrylate.

3. The process, according to claim 1, which is conducted in the presence of a thermal free-radical initiator.

4. The process, according to claim 1, wherein the concentration of said monomer or monomers 50 to 60 vol %.

5. The process, according to claim 1, wherein the reaction temperature is 45 to 100° C.

6. The process, according to claim 1, wherein the polymerization is carried out directly within a chromatography column in order to form a chromatographic packing material in situ.

7. The process, according to claim 1, wherein the monolith is chemically derivatised by flowing a solution of a chemical reagent in a solvent through the porous material.

8. The process, according to claim 7, wherein the solvent is supercritical carbon dioxide.

* * * * *